United States Patent [19]

Uriarte et al.

[11] 4,167,528

[45] Sep. 11, 1979

[54] PROCESS FOR THE PRODUCTION OF TETRABROMOETHYLENE

[75] Inventors: Anthony K. Uriarte; James H. Vaughan, both of Pensacola, Fla.

[73] Assignee: Monsanto Company, St. Louis, Mo.

[21] Appl. No.: 913,426

[22] Filed: Jun. 7, 1978

[51] Int. Cl.$^{2}$ .............................................. C07C 21/00

[52] U.S. Cl. ............................. 260/654 A; 252/455 Z

[58] Field of Search ....................... 260/654 H, 654 A; 252/455 Z

[56] References Cited

U.S. PATENT DOCUMENTS

| | | | |
|---|---|---|---|
| 3,363,010 | 1/1968 | Schwarzenbek | 260/662 A |
| 3,926,847 | 12/1975 | Beard et al. | 260/654 A |
| 3,987,118 | 10/1976 | Kuck | 260/662 A |
| 4,039,598 | 8/1977 | Uriarte | 260/654 H |

*Primary Examiner*—Delbert E. Gantz
*Assistant Examiner*—Joseph A. Boska
*Attorney, Agent, or Firm*—Thomas Y. Awalt, Jr.

[57] ABSTRACT

Tetrabromoethylene is produced by oxybrominating butane with free oxygen and bromine. The reaction is conducted in the gaseous phase, in the presence of a cupric bromide catalyst and the tetrabromoethylene is recovered by selective condensation of the reaction medium.

10 Claims, No Drawings

PROCESS FOR THE PRODUCTION OF TETRABROMOETHYLENE

BACKGROUND OF THE INVENTION

A. Field of the Invention

The invention relates to the production of tetrabromethylene from butane.

B. The Prior Art

The use of brominated organic intermediates to impart flame resistant properties to polymers is well established. Tetrabromoethylene has been described as useful as a fire retardant for styrene-type polymers (British Pat. No. 886,811). Heretofore, the production of tetrabromoethylene has been accomplished by the bromination of acetylene (Arm. Khim. Zh. 27 (8) 661 [1974]), bromination of ethylene (Nether. Applic. No. 6,510,390 [1966]) and the decomposition of sodium tribromoacetate (U.S. Pat. No. 3,274,270). In general, these methods give relatively poor selectivities to tetrabromoethylene.

An efficient process for the preparation for tetrabromoethylene in a single step from a readily available inexpensive raw material such as butane would constitute a significant advance in the art and is the primary object of this invention.

SUMMARY OF THE INVENTION

The invention is a process for the production of tetrabromoethylene from butane by oxybrominating the butane with free oxygen and bromine in the presence of a stabilized cupric bromide catalyst on a zeolite support having a selectively adsorptive structure corresponding generally to the adsorptivity of the natural zeolite faujasite, by feeding the oxygen, bromine and butane in gaseous phase into a reactor maintained under conditions of pressure and temperature corresponding to a temperature at atmospheric pressure of 250°to 300° C., in the pressure of the supported catalyst, so as to foster formation of the tetrabromoethylene in a reaction medium also comprising oxygen, bromine, unreacted butane and water. The product tetrabromoethylene may be recovered from the reaction medium by selective condensation.

DETAILED DESCRIPTION OF THE EMBODIMENT

As indicated above, the butane is oxybrominated with free oxygen and bromine in the presence of a cupric bromide catalyst. Only when the catalyst is presented to the reaction on a zeolite support, having the desired selectively adsorptive structure will the reaction proceed with a high degree of selectively to tetrabromoethylene.

Preparation of the supported catalyst involves saturation of the support with a solution of the catalyst. Known solvents for the catalyst are methanol and water. The solution ordinarily includes a stabilizer for the cupric halide. In this particular reaction, maintenance of stability of the catalyst is desirable for continuity of the reaction; and no other method of maintaining such stability than by the use of potassium bromide has been found. While the amount of the stabilizing salt is not critical, satisfactory results have been achieved employing stabilizing salts in the amount of 23-50% of the total weight of the catalyst mixture.

The solvent for the catalyst mixture is subsequently removed by filtration and/or evaporation as appropriate, and the support is dried under a nitrogen flow at about 150° C., to leave a catalyst mixture concentration of about 5-10% by weight based on the support.

The process is carried out in vapor phase, preferably in a fluidized or fixed-catalyst-bed reactor at 250-300° C. (atmospheric pressure). Temperatures in excess of about 300° C. should be avoided because excessive cracking and charring will result. At temperatures below about 250° C. there is little or no conversion of the butane.

The feed gases are preferably but not necessarily diluted with nitrogen so as to avoid the flammability region of the butane. Mole ratios of oxygen and bromine to butane of 0.1 to 2.5 and 0.1 to 4 respectively are workable with mole ratios of 0.1 to 0.5 and 0.1 to 0.5 respectively being preferred. Mole ratios of oxygen to butane of 0.8-4.9 and of air to butane of 1.9-8.5 should be avoided because of the danger of explosion at these ratios. Feed rates of the various components should be individually adjusted within the ranges set forth so as to provide maximum selectively of the tetrabromoethylene with respect to the particular apparatus employed, catalyst concentration, pressure and temperature.

As indicated above it is essential to this invention that the catalyst be supported on a zeolite support having a selectively adsorptive structure corresponding generally in adsorptivity to the natural zeolite faujasite. These supports have nominal pore sizes of about 10A°. Surprisingly, other types of supports, and particularly those supports having pore sizes substantially larger or smaller than the natural zeolite have been found to result in reactions producing significant percentages of compounds other than tetrabromoethylene.

Any convenient method of recovery of the tetrabromoethylene may be employed. Preferably the gaseous reaction mixture is selectively condensed at about 25° C. to remove the product tetrabromoethylene which will crystallize out with a high degree of purity.

EXAMPLE 1

(Preparation of the Catalyst)

A catalyst support of 80-100 mesh zeolite type 13X (pore size of 10 angstroms) was saturated with a 15% cupric bromide and 15% potassium bromide aqueous solution at reduced pressure (30 Torr). The resulting slurry was filtered and the residual solvent removed on a rotary evaporator.

EXAMPLE 2

(Preparation of Tetrabromoethylene)

The reactor employed was a 2X50-cm Pyrex Tube to which a gas inlet manifold was attached. A fluidized sand bed was used to maintain the temperature of the reactor. The reactor was charged with 30 cc (settled volume) of a catalyst consisting of 4.13% copper and 1.77% potassium (as bromide salts) on 80-100 mesh zeolite type 13X support (manufactured by Guild Corporation). Prepared as in Example 1 the reactor was maintained at 250° C. The gaseous reaction feed rates at 25° C. were n-butane at 100ml/minutes, oxygen at 50 ml/minutes, bromine at 15 ml/minutes or 0.1g $Br_2$/minutes and nitrogen at 500 ml/minutes. The contact time was 1.5 seconds. Reaction was continued for 2.2 hours, and the collected product was 9 grams reflecting a 70% bromine utilization. The clear product crystallized on standing, had a melting point of 50-54° C. It was found to contain 97% tetrabromoethylene and 2% pentabromoethane.

EXAMPLES 3-9

These examples are comparative examples, and were, except as otherwise indicated in Table I, conducted in the same manner as Example 2, the catalyst having been prepared generally as in Example 1. The results shown in the table reflect the surprisingly high selectivity to the tetrabromoethylene when the reaction is conducted using the specific zeolite support to which the invention is limited.

TABLE I

OXYBROMINATION OF BUTANE - $CuBr_2$ KBr ON SILICA AND ALUMINOSILICATES

| EX. | CATALYST COMPOSTION | SURFACE AREA m 2/g OF SUPPORT | PORE SIZE (A) OF SUPPORT | TEMP. °C. | RESID. TIME SEC. | GASEOUSFEED RATE AT 25° C., ml/min. $C_4H_{10}$ | $O_2$ | $Br_2$ | $N_2$ | RESULTS |
|---|---|---|---|---|---|---|---|---|---|---|
| 3 | 10% $CuBr_2$ + 3% KBr on (Girdler T-1571) Silica[$SiO_2$ (α quartz)] Carrier | 130 | 350–180000 | 250 | 5.1 | 100 | 50 | 23 | 400 | 80–90% selectivity to tetrabromobutadiene; others were lower brominated dienes |
| 4 | 10% $CuBr_2$ + 3% KBr on Girdler T-869 aluminosilicate carrier | 63 | 350–430000 | 270 | 4.5 | 100 | 50 | 24 | 400 | Much unreacted $Br_2$ at 250°. At 270° a complex mixture of polybrominated butanones a minor (< 10%) dibromobutenes. At 300° C., charring occurred. |
| 5 | Girdler T-869 carrier only | 63 | 350–430000 | 250 | 5 | 100 | 50 | 27 | 500 | Low conversion of $Br_2$ (~ 10%). $CO_2$ in off gas and small amount of brominated butanones. |
| 6 | 10% $CuBr_2$ + 3% KBr on montmorillonite $SiO_2$ (Girdler K-306) | 190 | 600–180000 | 250 | 4.8 | 100 | 50 | 24 | 400 | Complex mixture of brominated butanes and butanones. |
| 7 | 10% $CuBr_2$+ 5% NaBr on $SiO_2$ and $Al_2O_3$ . $SiO_2$ (Girdler T-869) | 63 | 350–430000 | 250 | 3.9 | 200 | 0 | 15 | 50 | ~ 60% dibromobutanes<br>~ 10-20% dibromobutenes |
| 8 | 10% $CuBr_2$ + 5% $NaBr_2$ on α-$Al_2O_3$ (Girdler T-708)<br>10% $CuBr_2$ on γ$Al_2O_3$ (Girdler T-126) | 130<br>5.3 | 350–1600<br>600–8000 | 275 | 5.5 | 200 | 0 | 45 | 50 | Product and catalyst turned black. |
| 9 | $CuBr_2$ + KBr on $Ca_{4.5}Na_3[(AlO_2)_{12}]$ . Molecular Sieves Type 5A | | 5 | 300 | 1.4 | 100 | 50 | 15 | 500 | $CuBr_2$ sublimed from catalyst - Product complex mixture of brominated butanes and butanones |

We claim:

1. Process for the oxybromination of butane in the production of tetrabromoethylene comprising reacting butane with free oxygen and bromine, at mole ratios of oxygen and bromine to butane of 0.1–2.5 and 0.1–4 respectively, all in gaseous phase, in the presence of a cupric bromide catalyst on a zeolite support having a selectively adsorptive structure corresponding generally to the adsorptivity of the natural zeolite faujasite, having a nominal pore size of about 10 angstroms, under conditions of pressure and temperature corresponding to temperatures at atmospheric pressure between 250°and 300° C. so as to foster formation of the tetrabromoethylene in a reaction medium also comprising oxygen, bromine unreacted butane and water.

2. The process of claim 1 wherein the catalyst is a mixture stabilized by inclusion therein of potassium bromide.

3. The process of claim 1 wherein the catalyst is supported by and impregnated in a zeolite Type 13X support having a composition in the amount of about 4–5% copper by weight of the catalyst based on the support.

4. The process of claim 1 wherein the selected condensation of an effluent of the reaction medium is conducted at a temperature of at least 25° C.

5. The process of claim 1 conducted at atmospheric pressure at a temperature of 250–300° C.

6. The process of claim 5 conducted at a temperature of 250° C.

7. The process of claim 1 wherein the product tetrabromoethylene is recovered by selective condensing of the reaction medium.

8. The process of claim 7 wherein the selective condensation is accomplished at a temperature of about 25° C.

9. The process of claim 1 conducted at mole ratios of oxygen and bromine to butane of 0.1–0.5 and 0.1–0.5 respectively.

10. The process of claim 1 wherein the catalyst is a mixture stabilized by inclusion therein of potassium bromide.

* * * * *